United States Patent [19]

Bair

[11] Patent Number: 4,717,729
[45] Date of Patent: Jan. 5, 1988

[54] TRIPHENYLENE DERIVATIVES

[75] Inventor: Kenneth W. Bair, Chapel Hill, N.C.

[73] Assignee: Burroughs Wellcome Co., Research Triangle Park, N.C.

[21] Appl. No.: 772,690

[22] Filed: Sep. 5, 1985

Related U.S. Application Data

[62] Division of Ser. No. 499,331, May 31, 1983, Pat. No. 4,551,282.

[51] Int. Cl.$^4$ .................. C07C 15/16; C07C 83/08; C07C 14.9/02; A61K 31/135
[52] U.S. Cl. .................. 514/654; 260/501.18; 260/501.19; 260/389; 260/386; 260/501.17; 560/255; 562/426; 564/387; 514/656; 514/908
[58] Field of Search .................. 260/501.18, 500.17, 260/389, 386, 501.19; 562/426; 560/255; 564/387; 514/654, 656, 908

[56] References Cited

U.S. PATENT DOCUMENTS

| | | | |
|---|---|---|---|
| 4,511,582 | 4/1985 | Bair | 514/654 |
| 4,530,800 | 7/1985 | Bair | 260/501.21 |
| 4,532,344 | 7/1985 | Bair | 560/252 |
| 4,551,282 | 11/1985 | Bair | 260/501.18 |

Primary Examiner—Glennon H. Hollrah
Assistant Examiner—Raymond Covington
Attorney, Agent, or Firm—Donald Brown

[57] ABSTRACT

The present invention relates to compounds of formula (I)

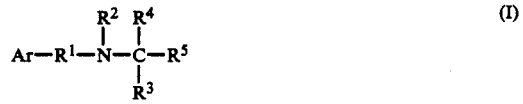

wherein
Ar is a triphenylene or substituted triphenylene ring system;
$R^1$ is a $C_{1-3}$ alkylene moiety;
$R^2$ is hydrogen or a $C_{1-6}$ alkyl group;
$R^3$ is a hydroxy $C_{1-6}$ alkyl group;
$R^4$ and $R^5$ are the same or different and are hydrogen, $C_{1-6}$ alkyl or hydroxy $C_{1-6}$ alkyl, esters thereof derived from condensation of carboxylic acids and hydroxyl groups of $R^3$, $R^4$, and $R^5$;

Acid addition salts thereof, which have been found useful for the treatment of tumors in mammals.

6 Claims, No Drawings

TRIPHENYLENE DERIVATIVES

This is a division of application Ser. No. 499,331, filed May 31, 1983, now U.S. Pat. No. 4,551,282.

The present invention relates to alkanol derivatives which have been found to be inhibitors of tumor growth. More specifically the invention concerns aminoalkanol derivatives containing a triphenylene or substituted triphenylene ring system, methods for the synthesis thereof, pharmaceutical formulations thereof, and the use thereof as antitumor agents.

There is accordingly provided, in a first aspect, compounds of the general formula (I)

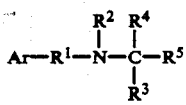
(I)

wherein
Ar is a triphenylene or substituted triphenylene ring;
$R^1$ is a $C_{1-3}$ alkylene moiety;
$R^2$ is hydrogen or a $C_{1-6}$ alkyl group;
$R^3$ is a hydroxy $C_{1-6}$ alkyl group;
$R^4$ and $R^5$ are the same or different and are hydrogen, $C_{1-6}$ are alkyl or hydroxy $C_{1-6}$ alkyl, esters thereof derived from condensation of carboxylic acids and hydroxyl groups of $R^3$, $R^4$, and $R^5$;
Acid addition salts thereof.

The side chain (i.e. as $-R^1-NR^2CR^3R^4R^5$) may be attached to the triphenylene ring system at any carbon atom where attachment is possible. For example, the side chain may be attached to the 2 position of a triphenylenyl moiety, although attachment to other positions of the triphenylene ring system is within the scope of the invention.

For antitumor activity the side chain defined by choice of $R^1$, $R^2$, $R^3$, $R^4$, and $R^5$ must not preclude in vitro intercalation by the resulting molecule of formula (I) to DNA. This property is determined using viscometric methods by the procedure of W. D. Wilson et. al., *Nucleic Acids Research* 4 2697 (1977).

In addition, the log P of the molecule as calculated by the method of C. Hansch and A. Leo in *Substituent Constants for Correlation Analysis in Chemistry and Biology*, John Wiley & Sons, New York, 1979, should normally lie in a range of acceptable values, most conveniently between $-2.0$ and $+2.5$.

$R^1$ is conveniently a straight chain $C_{1-3}$ alkylene moiety, e.g., methylene ($-CH_2-$).

$R^2$ is conveniently hydrogen but $C_{1-6}$ alkyl, e.g., methyl is also within the scope of the invention.

$R^3$ conveniently has the hydroxy group of the hydroxyalkyl group attached to an α carbon atom (i.e. the hydroxyl group is 2 carbon atoms removed from the nitrogen atom of the side chain). For example, $R^3$ may be hydroxymethyl ($-CH_2OH$).

While $R^4$ and $R^5$ may each be hydrogen, $C_{1-6}$ alkyl, or hydroxy $C_{1-6}$ alkyl, conveniently they are alkyl or hydroxyalkyl. Most conveniently at least one of $R^4$ and $R^5$ is hydroxyalkyl. When $R^4$ and/or $R^5$ is hydroxyalkyl the hydroxyl group is conveniently on an α carbon atom, for example hydroxymethyl ($-CH_2OH$).

The preferred side chain to be attached to the triphenylene ring system is that derived from 2-methyl-2-amino-1,3-propanediol (II)

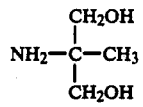
(II)

The triphenylene ring system may optionally bear one or more substituents known in the art to be advantageous to the pharmaceutical, pharmacological, or physical properties of a therapeutic agent when attached to an aromatic nucleus. Suitable subsitients include, for example, halogen (e.g. chloro, bromo), $C_{1-6}$ alkyl (e.g. methyl, ethyl), $C_{1-6}$ alkoxy (e.g. methoxy, ethoxy), halo $C_{1-6}$ alkyl (e.g. 2-chloroethyl, trifluoromethyl) $C_{1-6}$ alkylthio (e.g. thiomethyl and thioethyl), hydroxy$C_{1-6}$ alkyl (e.g., 2-hydroxyethyloxy) hydroxy $C_{1-6}$ alkylthio (e.g. 2-hydroxyethylthio), cyano, $C_{1-6}$ alkylsulphinyl, $C_{1-6}$ alkylsulphenyl; such substituents will not in general contain or comprise an aromatic moiety.

Such substituents may be attached to any appropriate position(s) on the triphenylene ring system.

Esters of compounds of formula (I) are conveniently those derived from $C_{1-6}$ alkanoic acids, e.g. acetic acid, propionic acid, n-butyric acid and isobutyric acid. Where the compound of formula (I) contains more than one hydroxyl group one or more of the hydroxyl groups may be esterified; however it is convenient that all hydroxyl groups are esterified.

Specific compounds within the scope of formula (I) include;
2-Methyl-2-((2-triphenylenylmethyl)amino)-1,3-propanediol, The compounds of formula (I) may be prepared by any method known in the art for the preparation of compounds of analogous structure. Thus the compounds of formula (I) may, for example, be prepared by any of the methods defined below.

1. Reductive amination of a compound of formula (III) with a compound of formula (IV):

(III)

$n = 0-2$

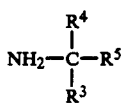
(IV)

wherein Ar, $R^1$, $R^2$, $R^3$, $R^4$ and $R^5$ are as defined herein above. The conditions and reagents for such a reaction are well known in the art of organic chemistry and any such conditions/reagents may be employed. For example, sodium cyanoborohydride ($NaBH_3CN$) conveniently comprises the reducing agent, and is used according to procedures outlined by R. O. Hutchins et. al., *Organic Preparations and Procedures International* 11 201 (1979).

2. Reduction of a compound of formula (V) also formed by reaction of compounds (III) and (IV): wherein Ar, $R^1$, $R^2$, $R^3$, $R^4$, and $R^5$ are as defined above.

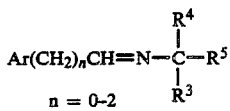

$$n = 0-2$$

The reducing agent may conveniently be LiAlH₄, NaBH₄, or hydrogen and a catalyst, or equivalent reagent as outlined by J. March, *Advanced Organic Chemistry*, 2nd ed., pages 682–683, McGraw Hill, New York, 1977. Compound (V) can also be made according to procedures outlined by J. March, vide supra page 667.

In turn, a compound of formula (III) (n=0) can be synthesised by reacting the appropriate triphenylene derivative with SnCl₄ and Cl₂CHOCH₃ or equivalent reagents, for example, according to the method A. Rieche et. al., *Chem. Ber.* 93, 88 (1960).

A compound of formula (III) (n=0) can also be synthesized by reacting the required triphenylene derivative with other appropriate formylating reagents/procedures known to the art, for example, as outlined by J. March, vide supra pages 416–420.

Appropriately substituted triphenylene derivatives may be converted to the corresponding aldehydes (III) (n=0–2) by any method known to the art.

Where the triphenylene ring bears substituents, the appropriate compound may in turn be prepared by a variety of methods known in the art of organic chemistry depending on the nature of the substituent on the ring. For example if the substituent(s) is a halogen, the starting materials may be prepared by direct treatment of the triphenylene derivative with a halogenating agent (e.g. Cl₂, Br₂, or SO₂Cl₂) or indirectly by such routes as the Sandmeyer reaction (D. T. Moury, *Chem. Rev.* 42 213 (1948)). If the substituent(s) is alkyl, the triphenylene derivative may be reacted with the appropriate reagents under Friedel-Crafts reaction conditions (P. Gore, *Chem. Rev.* 55 229 (1955)).

3. Reacting a compound of formula (VI) wherein R³, R⁴, and R⁵ are defined as above but at least one is H, and L is a leaving group as defined by J. March, vide supra pages 683 and 895, (e.g., Br, Cl, p-toluenesulfonate, etc.) with a compound of formula (VII).

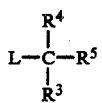

wherein Ar, R¹ and R² are as defined above.

A compound of formula (VII) can be synthesised by the method of reductive amination described above whereby reacting a compound of formula (III), and R²NH₂ (wherein R² is as defined above), in the presence of a reducing agent, for example sodium cyanoborohydride, or any other methods described in 2 or which are known to the art.

4. Reacting a compound of formula (VIII), wherein Ar, R¹, and L are defined $$Ar—R^1—L \quad (VIII)$$

as above with a compound of formula (IV) as defined above.

5. Reacting a compound of formula (IX), wherein Ar is defined above

and X is a halogen or equivalent leaving group with a compound of formula (IV) as defined above (preferably with any of the hydroxy group(s) appropriately protected) followed by reduction of the resulting amide with a reducing agent such as, for example, LiAlH₄ or equivalent agent. The reduction may be followed by deprotection if required. The compound of formula (IX) may be prepared by any of the widely known methods in the art for preparing similar compounds.

There is therefore provided, as a further aspect of the invention, a method for the preparation of a compound of formula (I) comprising any method known for the preparation of analogous compounds, in particular, those methods defined in (1) to (5) hereinabove.

The compounds of this invention have been found to have antitumor activity. Such activity is evidenced by reduction of tumor cell number in mammals bearing ascitic tumors and their consequent increase in survival duration as compared to a control group which is untreated. Antitumor activity is further evidenced by measurable reduction in the size of solid tumors in animals following treatment of the animal with the compounds of this invention compared to the tumors of untreated control tumor-bearing animals. The murine tumor lines against which the compounds of formula (I) are active include, but is not limited to, lymphocytic leukemia P388/0. Activity has also been demonstrated against sublines of the P388/0 which are resistant to a number of chemotherapeutic agents now in clinical use.

(As used herein "cancer" is to be taken as synonymous with "malignant tumor" or more generally "tumor" unless otherwise noted).

As has been described above, the compounds of the present invention are useful for the treatment of tumors. The invention thus further provides a method for the treatment of tumors in animals, including mammals, which comprises the administration of an effective, non-toxic amount of the compound of formula (I), an ester thereof, or an acid addition salt thereof, once, or several times a day orally, parenterally (including subcutaneous, intramuscular and intravenous), or applied topically. There is also provided as a further or alternative aspect of the invention, a compound of formula (I) for use in therapy, for example as an antitumor agent.

The amount of compound of formula (I) required to be effective as an antitumor agent will, of course, vary and is ultimately at the discretion of the medical or veterinary practitioner treating the mammal. The factors to be considered by such a practitioner, e.g., a physician, include; route of administration and pharmaceutical formulation; the mammal's body weight, surface area, age, and general condition; the particular salt or ester to be administered. However, a suitable effective antitumor dose is in the range of about 0.1 to about 120 mg/kg bodyweight, preferably in the range of about 1.5 to 50 mg/kg, e.g., 10 to 30 mg/kg. The total daily dose may be given as a single dose, multiple doses, e.g. two to six times p.d., or by intravenous infusion for any selected duration. For example, the dose range would be about 5 to 500 mg/kg per day. A typical dose for a 75 kg mammal would be about 2000 mg per day. If discrete multiple doses are indicated, treatment might typically be 500 mg of a compound of formula (I) given 4 times p.d. in the form of a tablet, capsule, liquid (e.g, syrup) or injection.

The antitumor activity of the compounds of formula (I) resides in the free base and thus the nature of the acid participating in the acid addition salts is of minor importance. However, when used in medicine, the salts of the compound of formula (I) should be both pharmacologically and pharmaceutically acceptable, but non-pharmaceutically and non-pharmacologically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulfuric, nitric, isethionic, phosphoric, maleic, salicyclic, p-toluenesulfonic, tartaric, lactic, citric, methanesulfonic, lactobionic, formic, malonic, pantothenic, succinic, naphthalene-2-sulfonic and benzenesulfonic.

While it is possible for the active compound (defined herein as compound of formula (I)) to be administered alone as the raw chemical, it is preferable to present the active compound as a pharmaceutical formulation. Formulations of the present invention, for medical use, comprise the active compound together with one or more pharmaceutically acceptable carriers thereof and optionally any other therapeutic ingredients. The carrier(s) must be pharmaceutically acceptable in the sense of being compatible with the other ingredients of the formulation and not deleterious to the recipient thereof.

The present invention therefore further provides a pharmaceutical formulation comprising a compound of formula (I) or an ester thereof (in the form of the free base or a pharmaceutically acceptable acid addition salt) together with a pharmaceutically acceptable carrier.

There is also provided a method for the preparation of pharmaceutical formulation which comprises bringing into association a compound of formula (I) or an ester thereof and a pharmaceutically acceptable carrier thereof.

The formulations include those suitable for oral, rectal, or parenteral (including subcutaneous, intramuscular, and intravenous injection) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets, or lozenges, each containing a predetermined amount of the active compound; as a powder or granules; or a suspension in an aqueous liquid or non-aqueous liquid such as a syrup, an elixir, an emulsion, or a draught. The active compound may also be presented as a bolus, electuary, or paste.

A tablet may be made by compression or molding, optionally with one or more accessory ingredients. Compressed tablets may be prepared by compressing in a suitable machine, the active compound in a free-flowing form such as a powder or granules, optionally mixed with a binder, lubricant, inert diluent, surfactant, or dispersing agent. Molded tablets may be made by molding in a suitable machine, a mixture of the powdered active compound with any suitable carrier.

A syrup may be made by adding the active compound to a concentrated, aqueous solution of a sugar for example sucrose to which may also be added any accessory ingredient. Such accessory ingredient(s) may include flavorings, an agent to retard crystallization of the sugar or an agent to increase the solubility of any other ingredient, such as a polyhydric alcohol (e.g. glycerol or sorbitol).

Formulations for rectal administration may be presented as a suppository with a usual carrier such as cocoa butter.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by the way of illustration of the present invention and should in no way be construed as a limitation thereof.

General Comments

All solvents were reagent grade and used without further purification with the following exceptions. THF was dried by distillation from Na/K alloy under $N_2$ and used immediately. Toluene ($PhCH_3$) was distilled from $CaH_2$ under $N_2$ and stored over 3 Å molecular sieves. Chemicals used were reagent grade and used without purification unless noted. The full name and address of the suppliers of the reagents and chemicals is given when first cited. After this, an abbreviated name is used.

Preparation HPLC was carried out on a Water's Prep LC/System 500 A machine using two 500 g silica gel ($SiO_2$) cartridges unless otherwise noted. Plugs of $SiO_2$ used for purifications were "flash chromatography" silica gel (E. Merck, silica gel 60, 230–400 mesh). An appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of $\leq 0.4\%$ of the expected value). Any changes to the procedure such as solvent, reaction temperature, reaction time, or workup are noted.

NMR ($^1H$, $^{13}C$), IR, MS data of all new products were consistent with the expected and proposed structures. The positions assigned to structural isomers were unequivocally determined by a number of NMR techniques. All final products were dried in a vacuum oven at 20 mm Hg pressure at the temperature indicated overnight (12–16 h). All temperatures are in degrees Celsius.

EXAMPLE 1

2-Methyl-2-((2-triphenylenylmethyl)amino)-1,3-propanediol, hydrochloride

A. 2-Triphenylenecarbaldehyde

A 1 L 3-neck flask fitted with overhead mechanical stirrer, thermometer, condenser, and $N_2$ line was charged with triphenylene (Aldrich Chemical Co., Milwaukee, WI, 53201, 30 g, 0.131 mol) and o-dichlorobenzene (150 mL). The liquid was warmed until all the large chunks of solid dissolved (80°) and then cooled quickly to give finely divided crystals. After further cooling with a salt-ice bath to 5°, $SnCl_4$ (Aldrich, 98%, 58 g, 0.223 mol, 26 mL), was added in one portion to the mixture. No temperature change occurred. The pot temperature was kept below 5°, and 1,1-dichloromethylmethylether (Aldrich, 25.6 g, 0.223 mol, 20 mL) was added dropwise over 1 h. The resulting suspension was warmed slowly to 40° over 2 h and further stirred for 16 h. Considerable HCl gas evolution occurred during the warming and the early part of the reaction at 40°. The reaction mixture was then cooled to 10° and hydrolysed by careful addition of 1 L of cold $H_2O$. After 4 h the layers were separated and the organic layer filtered, dried with anhydrous $Na_2SO_4$ (Mallinckrodt Co., 2nd and Mallinckrodt St., St. Louis, MO, 63147, 100 g) and filtered again. The solvent was removed to give a crude yellow oil which was purified by preparative HPLC using $PhCH_3$ as the eluting solvent. The fractions containing the aldehyde were combined and the solvent removed to give an oil which solidified (8.31 g, 25%). This material was used without further purification. Recrystallization from $CH_2Cl_2/CH_3OH$ gave pure 2-triphenylenecarbaldehyde mp 160°–161.5°, (C,H).

B. 2-Methyl-2-((2-triphenylenylmethyl)amino)-1,3-propanediol hydrochloride

To a 1 L Erlenmeyer flask was added 2-triphenylenecarbaldehyde 5.13 g, (20 mmol), 2-methyl-2-amino-1,3-propanediol (Aldrich, 2.2 g, 21 mmol), p-toluenesulfonic acid.$H_2O$ (Eastman Kodak Co., Rochester, NY, 14650, 0.1 g, 0.5 mmol), and $PhCH_3$ (250 mL). The mixture was warmed to reflux for a few minutes and $H_2O$ (2–3 mL) was driven off. The resulting golden colored solution was allowed to cool to RT, diluted with absolute EtOH (250 mL) and stirred overnight. $NaBH_3CN$ (Aldrich, 95%, 0.63 g, 10 mmol) was added to the reaction. After the $NaBH_3CN$ dissolved, an indicator (bromocresol green, Eastman, 5 mg) was added. To the resulting blue solution was added 5 drops of 1M solution of HCl gas in absolute EtOH every 15 minutes. After 3 days the indicator turned green then yellow and voluminous white precipitate was present in the flask. To the flask was then added 1M gas HCl (10 mL) in absolute EtOH. The reaction was diluted to 2 L with absolute ether and stirred for 1 h. The precipitate was then collected by filtration through a medium porosity glass fritted funnel and pressed dry. The filter cake was washed thoroughly with 20% HCL (2×250 mL), pressed dry and then washed with $CH_2Cl_2$ (4×500 mL), pressed and sucked dry. The crude off-white solid was then recrystallized (EtOH/$Et_2O$) 3× to give after drying (100°) 3.34 g (43%) of 2-methyl-2-((2-triphenylenylmethyl)amino)-1,3-propanediol hydrochloride.$\frac{1}{2}H_2O$ mp 207°–208.5° (dec), (C, H, Cl, N).

Antitumor Screening Results

Methods for evaluating the antitumor activity of these compounds are essentially those used in the Tumor Panel by the Developmental Therapeutics Program, Division of Cancer Treatment, National Cancer Institute, A. Goldin, et al., Methods in Cancer Research, Vol. XVI, p. 165, Academic Press (1979). Some modifications, in dose level and schedule have been made to increase the testing efficiency.

EXAMPLE 2

Lymphocytic Leukemia P388/0 Test $CD2$-$F_1$ mice, of the same sex, weighing within a 3 g range surrounding 20 g, are used for this test. Control and test animals are injected intraperitoneally with a suspension of ~$10^6$ viable P388/0 tumor cells on day 0. In each test several dose levels which bracket the $LD_{20}$ for the compound are evaluated; each dose level group contains 6 animals. The test compounds are prepared either in physiologic saline containing 0.05% Tween 80 or distilled water containing 5% dextrose and are administered intraperitoneally on days 1, 5, and 9 relative to tumor implant. Doses are on a mg/kg basis according to individual animals' body weights. The day of death for each animal is recorded, the median identified for each group and the ratios of median survival time for treated (T)/control (C) groups are calculated. The criterion for activity is T/C×100≧120%. The results of P388/0 testing are summarized in Table I below.

TABLE I

P388/0 Testing on Compound of Example 1

| Dose (mg/kg) | 30 Day Survivors | Median Day of Death | T/C × 100% | No Cells Surviving Therapy |
|---|---|---|---|---|
| 125 | 0/6 | 17.5 | +175 | Toxic |
| 84 | 0/6 | 20.0 | +200 | $1.9 \times 10^5$ |
| 56 | 0/6 | 17.0 | +170 | $2.7 \times 10^7$ |
| Untreated Controls | 0/6 | 10 | — | — |

EXAMPLE 3

Formulation Examples

| A. TABLET | |
|---|---|
| Compound of Formula I | 500.0 mg |
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

| B. TABLET | |
|---|---|
| Compound of formula (I) | 500.0 mg |
| Corn Starch | 70.0 mg |
| Lactose | 83.8 mg |
| Magnesium Stearate | 4.2 mg |
| Polyvinylpyrrolidone | 14.0 mg |

-continued

| B. TABLET | |
|---|---|
| Stearic Acid | 28.0 mg |

The compound of formula (I) is finely ground and intimately mixed with the powdered excipients, corn starch and lactose. The powders are wetted with a solution of polyvinylpyrrolidone dissolved in purified water and denatured alcohol to form granules. The granules are dried and mixed with the powdered stearic acid and magnesium stearate. The formulation is then compressed into tablets weighing approximately 700 mg each.

| C. CAPSULES | |
|---|---|
| Compound of formula (I) | 500.0 mg |
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shell gelatin capsules.

| D. SYRUP | |
|---|---|
| Compound of formula (I) | 250.0 mg |
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water q.s. to | 5.0 ml |

The compound of formula (I) is dissolved in the ethanol, glycerin, and a portion of the purified water. The sucrose and preserving agent are dissolved in another portion of hot purified water, and then the coloring agent is added and dissolved. The two solutions are mixed and cooled before the flavoring agent is added. Purified water is added to final volume. The resulting syrup is throughly mixed.

| E. IV INJECTION | |
|---|---|
| Compound of formula (I) | 5.0 mg |
| Glycerin | q.s. for isotonicity |
| Preservative | 0.1% |
| Hydrochloric Acid or Sodium Hydroxide | as needed for pH adjustment |
| Water for Injection | q.s. to 1 ml |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 ml ampules or vials.

What is claimed is:

1. A pharmaceutical formulation containing a compound of formula (I)

$$Ar-R^1-N(R^2)-C(R^3)(R^4)-R^5 \quad (I)$$

wherein

Ar is triphenylene or triphenylene substituted with halogen, $C_{1-6}$ alkyl, $C_{1-6}$ alkoxy, halo $C_{1-6}$ alkyl, $C_{1-6}$ alkylthio, hydroxy $C_{1-6}$ alkyl, hydroxy $C_{1-6}$ alkylthio, cyano, $C_{1-6}$ alkylsulphinyl or $C_{1-6}$ alkylsulphenyl;

$R^1$ is $C_{1-3}$ alkylene;

$R^2$ is hydrogen or $C_{1-6}$ alkyl;

$R^3$ is hydroxy $C_{1-6}$ alkyl; and $R^4$ and $R^5$ are the same or different and are hydrogen, $C_{1-6}$ alkyl or hydroxy $C_{1-6}$ alkyl, or a $C_{1-6}$ alkylcarboxylic acid ester derived therefrom or a pharmaceutically acceptable acid addition salt thereof together with a pharmaceutically acceptable carrier therefor.

2. A pharmaceutical formulation of claim 1 wherein the compound of formula (I) is 2-methyl-2-((2-triphenylenylmethyl)amino)-1,3-propanediol hydrochloride.

3. A pharmaceutical formulation of claim 1 in the form of an injection.

4. The method of reducing the number of cells of a susceptible tumor which comprises contacting said susceptible tumor cells with a compound of the formula $$Ar-R^1-N(R^2)-C(R^3)(R^4)-R^5$$

wherein

Ar is triphenylene or a triphenylene ring system substituted with halogen, $C_{1-6}$ alkyl, $C_{1-6}$ alkoxy, halo $C_{1-6}$ alkyl, $C_{1-6}$ alkylthio, hydroxy $C_{1-6}$ alkyl, hydroxy $C_{1-6}$ alkylthio, cyano, $C_{1-6}$ alkylsulphenyl or $C_{1-6}$ alkylsulphinyl, $R^1$ is $C_{1-3}$ alkene, $R^2$ is hydrogen or $C_{1-6}$ alkyl;

$R^3$ is hydroxy $C_{1-6}$ alkyl; and $R^4$ and $R^5$ are the same or different and are hydrogen, $C_{1-6}$ alkyl or hydroxy $C_{1-6}$ alkyl or a $C_{1-6}$ alkyl carboxylic acid ester thereof or a pharmaceutically acid addition salt thereof.

5. The method of claim 4 in which 2-methyl-2-triphenylenylmethyl)amino)-1,3-propanediol or a pharmaceutically acceptable salt thereof is used to contact said susceptible tumor cells.

6. A pharmaceutical formulation which comprises 2-methyl-2-((2-triphenylenylmethyl)amino)-1,3-propanediol or a pharmaceutically acceptable salt thereof together with a pharmaceutically acceptable carrier therefor.

* * * * *